(12) United States Patent
Band et al.

(10) Patent No.: US 7,231,250 B2
(45) Date of Patent: Jun. 12, 2007

(54) METHOD AND APPARATUS FOR THE SETTING OR ADJUSTMENT OF A CARDIAC PACEMAKER

(75) Inventors: David Marston Band, Surrey (GB); Terence Kevin O'Brien, Cambridgeshire (GB); Christopher Bancroft Wolff, Cambridgeshire (GB)

(73) Assignee: Lidco Group Plc, London (GB)

( * ) Notice: Subject to any disclaimer, the term of this patent is extended or adjusted under 35 U.S.C. 154(b) by 285 days.

(21) Appl. No.: 10/506,612

(22) PCT Filed: Mar. 11, 2003

(86) PCT No.: PCT/GB03/01001

§ 371 (c)(1),
(2), (4) Date: Sep. 13, 2004

(87) PCT Pub. No.: WO03/077991

PCT Pub. Date: Sep. 25, 2003

(65) Prior Publication Data

US 2005/0154422 A1    Jul. 14, 2005

(30) Foreign Application Priority Data

Mar. 12, 2002 (GB) ................................ 0205771.9

(51) Int. Cl.
*A61N 1/365* (2006.01)
(52) U.S. Cl. .......................................... 607/18; 607/20
(58) Field of Classification Search ............. 607/17–20
See application file for complete search history.

(56) References Cited

U.S. PATENT DOCUMENTS

| | | | |
|---|---|---|---|
| 3,584,618 A * | 6/1971 | Reinhard et al. ............ 600/536 |
| 5,540,727 A * | 7/1996 | Tockman et al. ............. 607/18 |
| 5,964,788 A | 10/1999 | Greenhut | |
| 5,995,870 A | 11/1999 | Cazeau et al. | |
| 6,071,244 A * | 6/2000 | Band et al. .................. 600/526 |
| 6,141,590 A * | 10/2000 | Renirie et al. ................ 607/20 |
| 6,275,727 B1 | 8/2001 | Jones et al. | |

FOREIGN PATENT DOCUMENTS

| | | |
|---|---|---|
| EP | 1 155 711 A2 | 11/2000 |
| EP | 1 192 971 A2 | 4/2002 |
| WO | WO 99/02086 * | 1/1999 |
| WO | WO 99/30777 A1 | 6/1999 |
| WO | 01 32260 A | 5/2001 |

\* cited by examiner

*Primary Examiner*—Robert E. Pezzuto
*Assistant Examiner*—Eric D. Bertram
(74) *Attorney, Agent, or Firm*—Bacon & Thomas PLLC

(57) ABSTRACT

A method of setting or adjusting a cardiac pacemaker in a patient diagnosed with cardiac asynchrony, which method comprises the steps of: i) implanting cardiac pacing wires into at least the right ventricle and the left ventricle of the heart of the patient, ii) continuously monitoring and recording the cardiac output, nominal stroke volume and/or arterial pressure of the patient on a beat-by-beat basis, iii) continuously monitoring and recording the respiratory cycle of the patient, and iv) adjusting the conduction delay between the electronic impulses to the cardiac pacing wires until a synchronization of respiratory changes with changes in the cardiac output, stroke volume or arterial pressure of the patient is obtained.

23 Claims, 3 Drawing Sheets

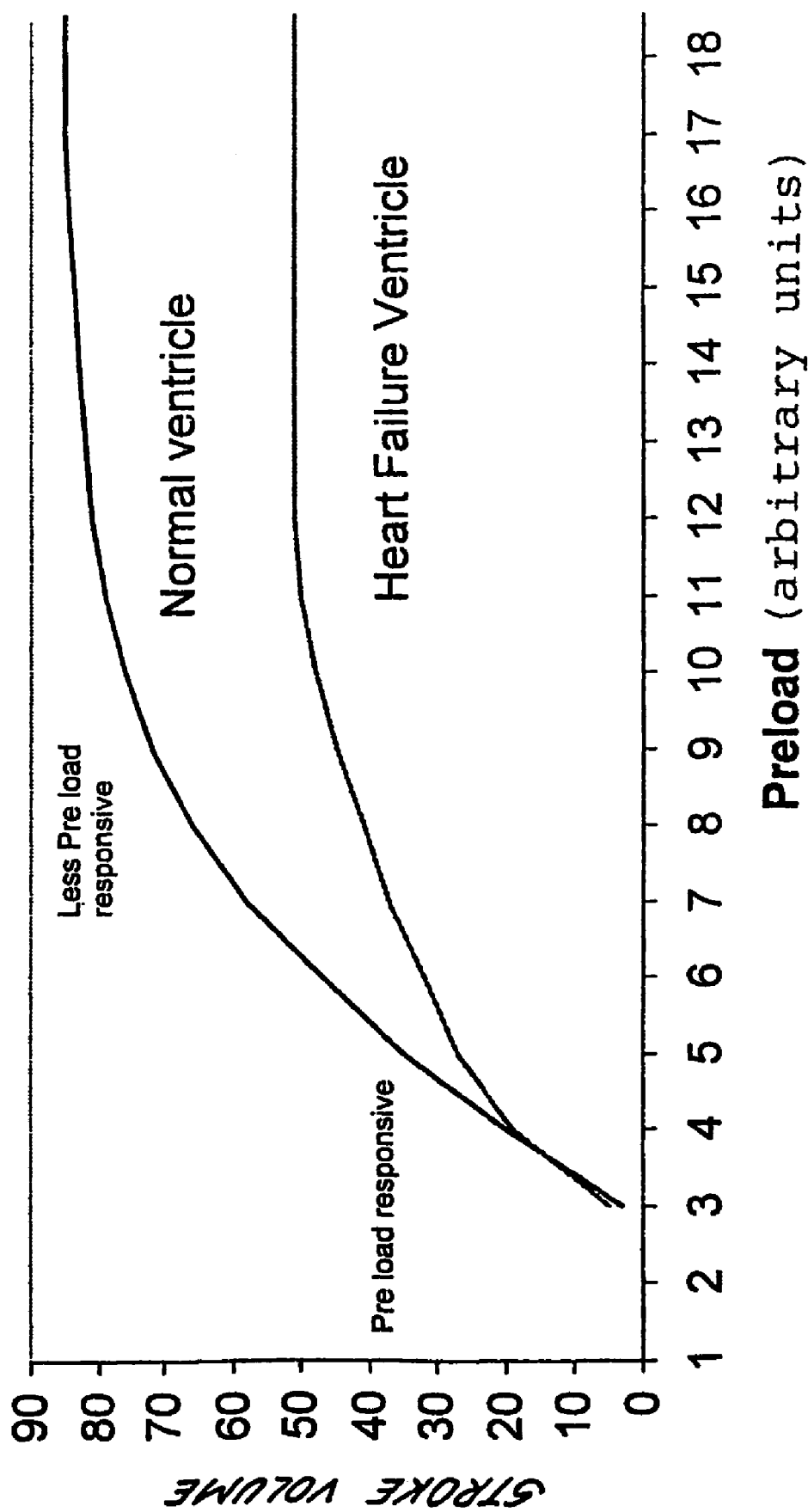

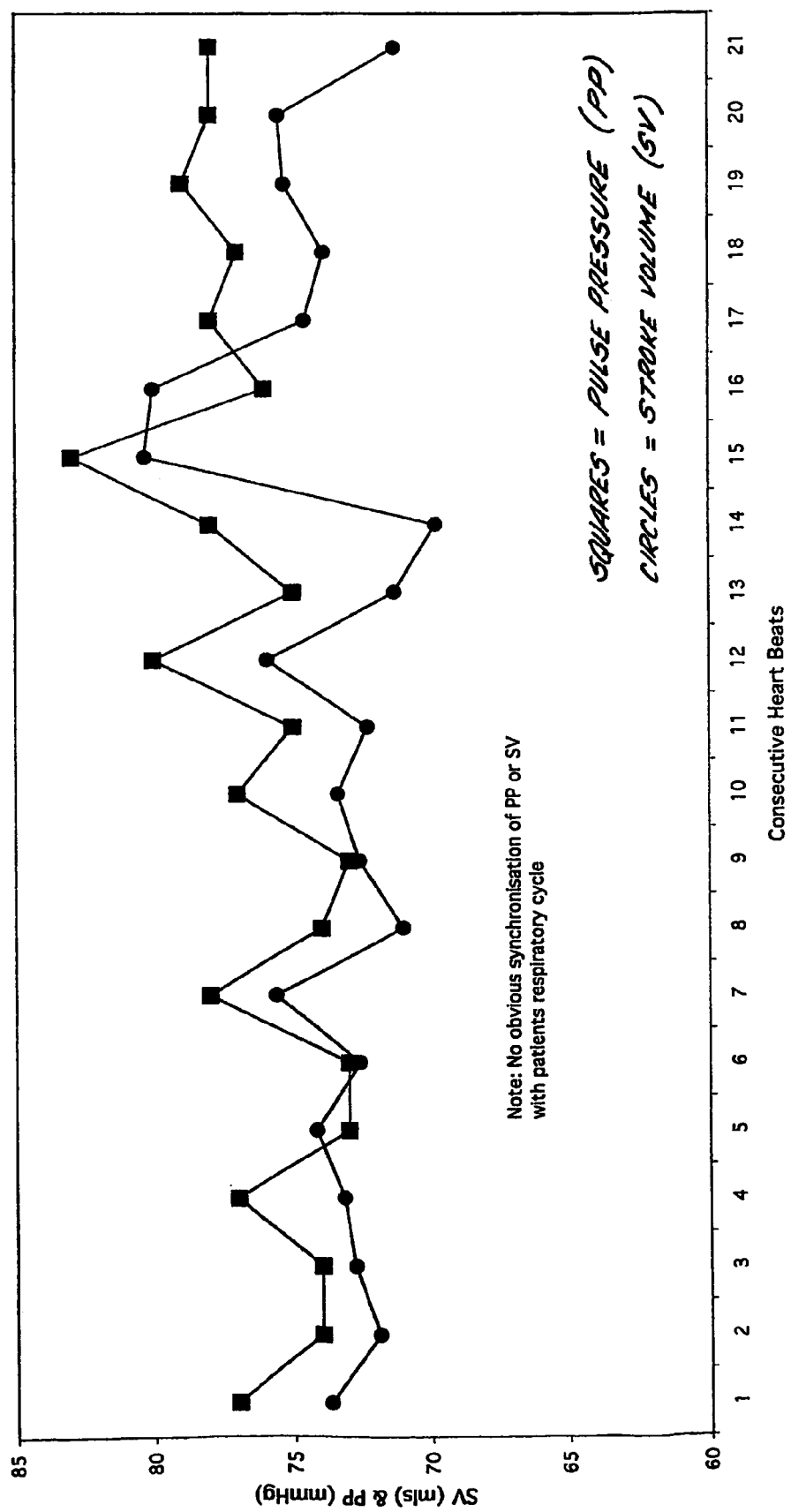

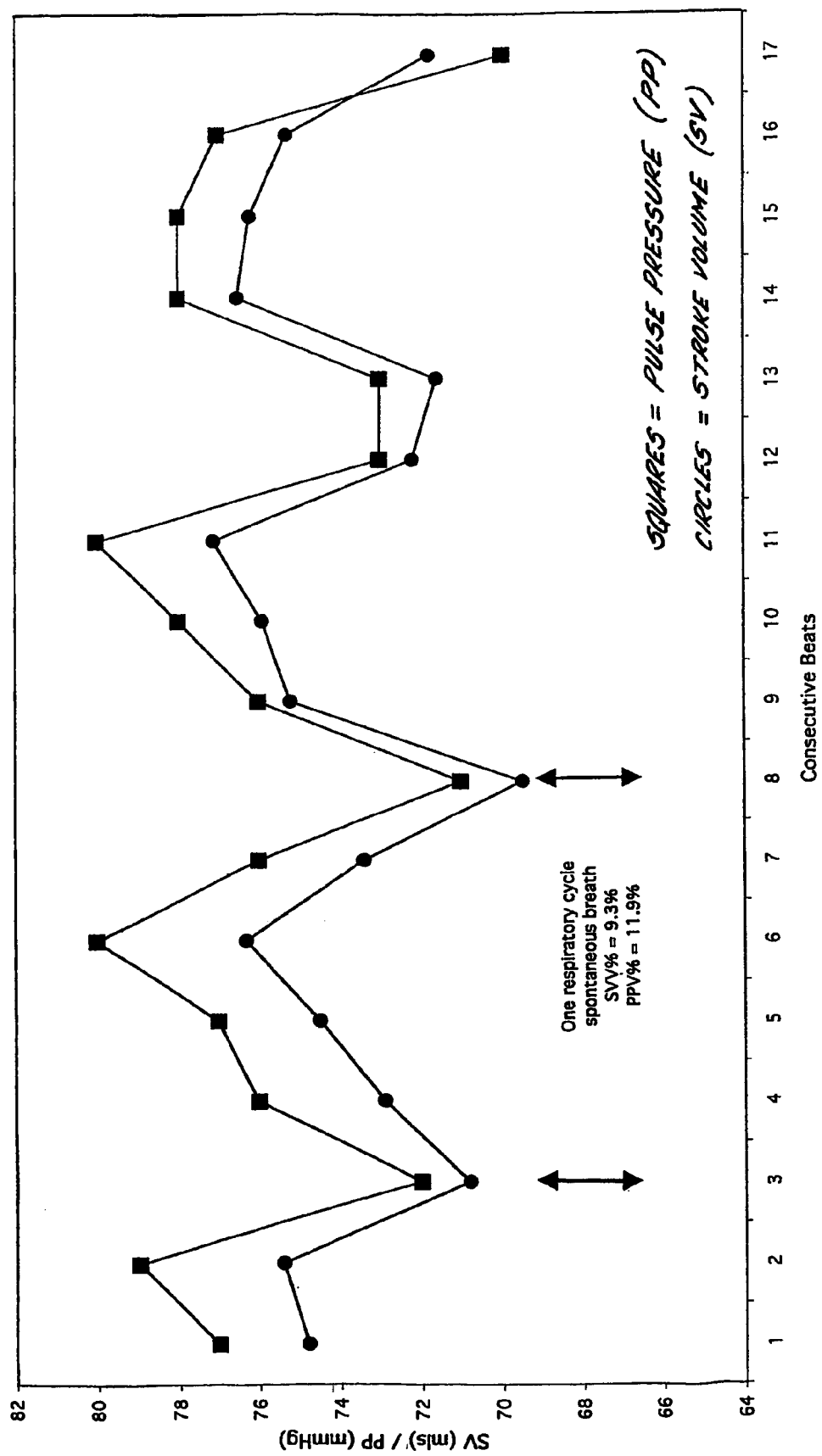

METHOD AND APPARATUS FOR THE SETTING OR ADJUSTMENT OF A CARDIAC PACEMAKER

The present invention relates to a method and apparatus for the setting or adjustment of a cardiac pacemaker and, in particular, to the setting or adjustment of a cardiac pacemaker in a patient diagnosed with asynchrony.

Cardiac heart failure is a syndrome which is associated with ill health and death, despite continuing advances in drug therapy. It has been found that many congestive heart failure (CHF) patients have a common pathology whereby the left ventricle (the side which supplies blood to the body) is not contracting in synchrony with the other chambers of the heart. For example, it may contract during left atrial filling and/or after right ventricular diastole begins. This can lead to reduced left ventricular filling and mitral valve regurgitation. These patients usually have an increase in blood pressure(s) on the left side of the heart, with the resulting progressive distension of the left ventricle wall, consequent failing left heart performance and ultimately death.

Standard dual chamber pacemakers which pace and synchronise the right atrium and the right ventricle do not appear to improve the condition of patients with New York Heart Association (NHYA) Class III and Class IV heart failure—they are not therefore of use in the management of CHF. It has been thought that the efficacy of the heart in CHF patients could be increased or restored if the start of the ventricular systole could be synchronised by pacing the right atrium of the heart followed by the right ventricle and left ventricle. This technique is known as biventricular pacing, or resynchronisation therapy. However, from the various studies which have been carried out it is clear that while some patients respond remarkably, for many patients there is no significant improvement. Studies in respect of biventricular pacing in congestive heart failure patients are described in, for example, Morris Thurgood, J. A. and Frenneaux, M. P.; Pacing in Congestive Heart Failure, Current Controlled Trials in Cardiovascular Medicine 2000; 1(2): 107–114 and Haywood, G; Biventricular pacing in heart failure: update on results from clinical trials, Current. Controlled Trials in Cardiovascular Medicine 2001; 2(6): 292–297.

It is clear that considerable uncertainty exists as to how exactly biventricular pacing actually works, which CHF patients will respond and whether the benefits of biventricular pacing are better than left ventricular pacing only. One problem is that the restoration of synchrony of the left and right ventricles of the heart is very difficult to demonstrate clinically in the catheterisation laboratory. Early studies used echocardiography and radionucleotide angioscintigraphy (radioactivity injection into the heart with the ventricle being subsequently visualised by use of a gamma camera.) These techniques are complex, invasive and costly. Equally blood flow measurements with a thermodilution (bolus or continuous) catheter and/or Doppler ultrasound are also invasive and limited in terms of adequately demonstrating the restoration of normal cardiac physiology. Finally, resolution of small and possibly not persistent, changes in blood flow demand a non or minimally invasive monitoring system with the ability to resolve small (<2%) real time changes in stroke volume.

It has therefore previously been very difficult to ascertain whether or not fitting a biventricular cardiac pacemaker to a CHF patient actually improves the cardiac function.

Furthermore, the clinician is not only trying to restore cardiac synchrony but to optimise the left ventricle response to preload, i.e. to set the heart rate and conductive delays of the pacemaker wires that allow for the most efficient provision of both normal and demand responsive systemic tissue oxygen delivery.

The extent to which the ventricle is filled pre the systolic contraction influences the ejected volume (stroke volume) of that beat (Starling mechanism.) Essentially, the more the ventricle is filled before the contraction phase, the more work is done ejecting blood by that contraction. This is true i.e. there is a linear relationship only up to a certain maximum filling pressure at which the ventricle becomes less responsive. Changes in the intra thoracic pressure in positive pressure ventilated patients cause changes to the filling pressure of the left ventricle which, through the Starling mechanism, results in differing pre systolic left ventricular end diastolic volume. This results in small (but measurable by arterial waveform analysis) respiratory driven cyclical changes in the ejected stroke volume. The magnitude of the stroke volume variation across the respiratory cycle and/or the resultant arterial pulse pressure (pulse pressure variation %—PPV %) are useful parameters and are known to accurately predict the likely response of the left ventricle to additional fluid administration in positive pressure ventilated patients.

Therefore the magnitude of respiratory induced blood flow and pressure changes can be used to predict the likely response to increased venous return. Clinically this technique is mostly used in mechanically ventilated critical care patients in conjunction with stroke volume and cardiac output measurements to optimise the cardiovascular status of the patient.

Less well known is that in spontaneously breathing patients without CHF cyclical changes in these parameters is also exhibited. Thus, during inspiration (breathing in) the diaphragm of the patient moves down, thereby decreasing the intra thoracic pressure and increasing the venous filling and stroke volume of the heart. During expiration (breathing out) the diaphragm of the patient moves up, thereby increasing the intra thoracic pressure and decreasing the venous filling and stroke volume of the heart. In spontaneously breathing patients with CHF this normal physiological pattern is not generally displayed. We have now realised that advantage could be taken of the changes of stroke volume or arterial pulse pressure across the respiratory cycle in order to determine whether or not a CHF patient is responding to the insertion and setting of a cardiac pacemaker in the heart.

Accordingly, the present invention provides a method of setting or adjusting a cardiac pacemaker in a patient diagnosed with cardiac asynchrony, which method comprises he steps of:

i) implanting cardiac pacing wires into at least the right ventricle and the left ventricle of the heart of the patient, ii) continuously monitoring and recording the cardiac output, nominal stroke volume and/or arterial pressure of the patient on a beat-by-beat basis, iii) continuously monitoring and recording the respiratory cycle of the patient, and iv) adjusting the conduction delay between the electronic impulses to the cardiac pacing wires until a synchronization of respiratory changes with changes in the cardiac output, stroke volume or arterial pressure of the patient is obtained.

In carrying out the present invention, the respiratory cycle of the patient can be recorded visually, or preferably by means of computer analysis of the arterial waveform, or by means of a strain gauge placed around the patient's chest.

The nominal stroke volume may be obtained using an adaptation of the method described in WO 97/24982 or WO 99102086 for measuring cardiac output in a patient. In both of these methods the nominal stroke volume is calculated and the cardiac output obtained by multiplying the stroke volume by the heart rate.

The nominal stroke volume is uncalibrated data and may be converted into calibrated data, if desired, by multiplying the nominal stroke volume by a calibration actor to give the true stroke volume.

Accordingly, in a first aspect of the present invention the nominal stroke volume may be obtained by a method which comprises the steps of:
 (a) recording and storing the arterial blood pressure waveform of a patient from a blood pressure monitoring device over a period of time;
 (b) subjecting the waveform obtained in step (a) to a non-linear transformation that corrects for the variation of the characteristics of the arterial system with pressure;
 (c) subjecting the corrected waveform from step (b) to autocorrelation in order to derive the pulsatility and heart rate of the corrected waveform; and
 (d) calculating the nominal stroke volume from the pulsatility.

In a second aspect of the present invention the nominal stroke volume may be obtained by a method which comprises the steps of:
 (e) recording and storing the arterial blood pressure waveform of a patient from a blood pressure monitoring device over a period of time;
 (f) subtracting the mean of the waveform from step (e) and subjecting the data so obtained to autocorrelation;
 (g) transforming the data from step (f) into data which relates to the pulsatility and heart rate of the waveform; and
 (h) calculating the nominal stroke volume from the pulsatility.

In a third aspect of the present invention the nominal stroke volume may be obtained by a method which comprises the steps of:
 (i) recording and storing the arterial blood pressure waveform of a patient from a blood pressure monitoring device over a period of time;
 (j) subjecting the data obtained in step (i) to Fourier analysis in order to obtain the modulus of the first harmonic; and
 (k) determining the nominal stroke volume from the modulus of the first harmonic obtained in step (j) and data relating to the arterial blood pressure and the heart rate.

In a fourth aspect of the present invention the nominal stroke volume may be obtained by a method which comprises the steps of:
 (l) recording and storing the arterial blood pressure waveform of a patient from a blood pressure monitoring device over a period of time;
 (m) subjecting the waveform obtained in step (l) to a non-linear transformation that corrects for the variation of the characteristics of the arterial system with pressure;
 (n) subjecting the data obtained in step (m) to Fourier analysis in order to obtain the modulus of the first harmonic;
 (o) determining the nominal stroke volume from the modulus of the first harmonic obtained in step (n) and data relating to the heart rate and optionally the arterial blood pressure.

In the first and fourth methods for obtaining the nominal stroke volume the pressure waveform is preferably transformed via a "look up" curve, with the mean of the data then being found and subtracted, into data which represents the pressure/volume relationship of the arterial system. The basic approximation to a look up table is known in the art and the relationship is non-linear, a series of such curves being described in Remington et al, 1948, Am. J. Physiol 153: 298–308; Volume elasticity characteristics of the human aorta and prediction of the stroke volume from the pressure pulse.

In the first method for obtaining the nominal stroke volume, the corrected waveform from step (b) is subjected to autocorrelation in order to determine the pulsatility and heart rate of the transformed waveform. Autocorrelation is defined in Dictionary of Science and Technology, Academic Press, 1992, p 186. The technique of autocorrelation is known in the art and is further described in detail in WO 97/24982.

In the second method for obtaining the nominal stroke volume, the autocorrelation is carried out on the arterial blood pressure data after subtraction of the mean of the waveform. The autocorrelation data is then transformed into data which relates to the pulsatility and heart rate of the waveform.

In the third and fourth methods for obtaining the stroke volume the arterial blood pressure waveform of the patient, which may be subjected to a non-linear transformation that corrects for the variation of the characteristics of the arterial system with pressure, is subjected to a Fourier analysis in order to obtain the modulus of the first harmonic. Fourier analysis is known in the art and may be used to determine the harmonic components of a complex name and is described in detail in many mathematical and physics textbooks. Fourier analysis is also described in more detail in WO 99/02086.

In carrying out the various methods for obtaining the nominal stroke volume the patient's arterial blood pressure is monitored continuously by conventional means from, for example, the aorta, the brachial artery or radial artery. Accordingly, the patient's arterial blood pressure may be monitored using an arterial catheter with a transducer system or a non-invasive method. The output from the pressure measuring device provides the blood pressure over a period of time.

It will be understood that in carrying out the method of the present invention the changes in the arterial pressure may be monitored instead of the changes in the stroke volume and used to indicate when there is a synchronization between the respiratory cycle and heart function. The systolic or diastolic pressures may be monitored or preferably the arterial pulse pressure (systolic pressure minus diastolic pressure) is monitored.

Preferably in carrying out the present invention a third cardiac pacing wire is additionally implanted into the right atrium of the patient's heart.

The adjustment of the conduction delays between the individual electronic impulses to the different cardiac pacing wires may be adjusted systematically using a pre-determined matrix. As the conduction delays are varied, the changes of cardiac output, stroke volume or arterial pressure are monitored and recorded. The conduction delays may be varied until a sufficient asynchrony of the heart is obtained such that there are observable respiratory derived changes in cardiac output, stroke volume and/or arterial pressure.

The method of the present invention also includes the possibility of the pacing rate of the electronic impulses to the cardiac pacing wires being varied. For example the pacing rate may be varied between 40 and 100 beats per minute, preferably between 80 and 100 beats per minute.

In carrying out the method of the present invention the cardiac output, nominal stroke volume and/or arterial pressure and the respiratory cycle of the patient will preferably be recorded and stored in an appropriately programmed computer and displayed upon a display device integral with, or connected to, the computer. A cardiovascular monitoring device that uses the radial arterial waveform to derive and store real time blood pressure, cardiac output and stroke volume data is the PulseCo System available from LiDCO Ltd., London, United Kingdom. This device can be modified so as to simultaneously record and store information in respect of the respiratory cycle of the patient. With the real time respiratory cycle data superimposed upon the same display screen as the real time information in relation to blood pressure, cardiac output and stroke volume, it is easy to see when there is synchronization of the changes in nominal stroke volume or arterial pressure over time with the respiratory cycle.

The general theory upon which the present invention is predicated may also be used to adjust cardiac pacemakers which are already implanted into a subject's heart in order to improve or adjust the settings thereof.

Accordingly, in a still further aspect the present invention provides a method of adjusting a cardiac pacemaker having cardiac pacing wires implanted into at least the right ventricle and the left ventricle of the heart of a subject, which method comprises the steps of:

(x) continuously monitoring and recording the cardiac output, nominal stroke volume and/or arterial pressure of the subject on a beat-by-beat basis, (xi) continuously monitoring and recording the respiratory cycle of the patient, and (xii) adjusting the conduction delay between the electronic impulses to the cardiac pacing wires until a synchronization of respiratory changes with changes in the cardiac output, stroke volume or arterial pressure of the subject is obtained.

The manner in which the previously implanted pacemakers may be adjusted follows the general teaching above in relation to the settings or adjustment of cardiac pacemakers in a patient diagnosed with asynchrony.

The present invention also includes within its scope an apparatus for setting or adjusting a cardiac pacemaker in a patient diagnosed with asynchrony and having cardiac pacing wires implanted into at least the right ventricle and the left ventricle, which apparatus comprises:

(A) means for continuously monitoring and recording the cardiac output, nominal stroke volume and/or arterial pressure of the patient;

(B) means for continuously monitoring and recording the respiratory cycle of the patient;

(C) means for adjusting the delay between the electronic impulses to the pacing wires; and (D) means for determining when a synchronization of the respiratory changes with changes in the cardiac output, stroke volume or arterial pressure is obtained.

The method of the present invention not only enables the clinician to select appropriate settings for a cardiac pacemaker to reduce asynchrony or restore synchrony in a patient, but also to select settings for the particular patient which optimise cardiac output and oxygen delivery.

Furthermore, when synchrony of the left ventricle has been restored the subsequent determination of changes in cardiac output, stroke volume or arterial pressure can be used as indicators of pre-load responsiveness. These changes can be observed by measuring the respiratory driven beat to beat changes of cardiac output, stroke volume and/or arterial pressure. The present invention is further described by reference to the accompanying drawings, in which:

FIG. 1 illustrates the Frank-Starling's curve which plots stroke volume against preload (in arbitrary units;

FIG. 2 illustrates for the patient of the Example the lack of correlation in the respiratory cycle with changes in stroke volume and the pulse pressure before activation of the pacemaker; and FIG. 3 illustrates for the patient of the Example the correlation in the respiratory cycle with changes in pulse pressure and stroke volume with the pacemaker activated at a heart rate of 80 beats per minute and an atrium to ventricle delay of 80 msec.

Referring to FIG. 1, the best pacemaker settings can be chosen so as to maintain an appropriate cardiac output whilst keeping the patient on the most vertical portion of the ventricular Starling curve as illustrated. Thus, the heart rate and conduction delays of the electronic impulses to the individual pacing wires can be chosen so as to provide the most efficient (least work) forward blood flow.

The potential clinical application of the present invention include:

Improved patient screening for biventricular pacing suitability—if following the implantation of the pacemaker leads respiratory variations cannot be shown the ventricle may not be capable of responding to this therapy and the cost of the pacer can be avoided.

Epicardial lead placement optimisation—placement of the pacemaker leads may be further optimised by this technique.

Optimisation of pacer settings in terms of time taken to demonstrate resynchronisation, appropriate heart rate and various chamber delays and ventricle pre load responsiveness.

Following setting of the pacemaker, appropriate feedback during a stress and/or exercise test may be obtained in order that the pacemaker settings may be optimised.

The present invention will be further described with reference to the following Example.

EXAMPLE

A Clinical Example of the Use of Respiratory Driven Changes in Haemodynamic Parameters as a Predictor of Ventricle Synchrony and Pre Load Responsiveness A male patient age 57 with NYHA Class III chronic heart failure and was implanted with a biventricular pacer for the improvement of his asynchrony. The setting of the pacer was monitored with use of a cardiovascular monitoring device (Pulse Co System—LiDCO Ltd, London, UK) that uses the radial arterial pressure waveform to derive and store real time blood pressure, cardiac output and stroke volume data. The pacer was a Guidant biventricular pacer in which the left and right ventricular wires are physically joined together and therefore electronic impulses to the right ventricle and left ventricle occur at the same time and cannot be varied.

FIG. 2 illustrates the lack of correlation of the patient's respiratory cycle with the changes in stroke volume and pulse pressure before the activation of the pacemaker.

FIG. 3 illustrates the correlation of the respiratory changes in arterial pulse pressure and stroke volume in this patient with the pacemaker being activated at a heart rate of 80 beats per minute and with an atrium to ventricle delay of 80 msec.

Various atrium to ventricle conduction delays were applied to this patient at two different heart rates and the results are given in Table 1 below:

| Atrium to Ventricle Delay (msec) at 80 bpm | | | | | | |
|---|---|---|---|---|---|---|
| 40 | 80 | 100 | 110 | 120 | 150 | Pacer off |
| Cardiac Output (1/min) | | | | | | |
| 5.4 | 5.8 | 5.8 | 5.9 | 6 | 6 | 5.6 |
| Stroke Volume (ml) | | | | | | |
| 67.5 | 72.5 | 72.5 | 73.75 | 75 | 75 | 75 |
| Stroke Volume Variation (%) | | | | | | |
| 11 | 11 | 11 | 10 | 10 | 11 | N/a |

| Atrium to Ventricle Delay (msec) at 90 bpm | | | | |
|---|---|---|---|---|
| 40 | 80 | 100 | 110 | Pacer Off |
| Cardiac Output (1/min) | | | | |
| N/a | 6.7 | 7 | 7.2 | 5.6 |
| Stroke Volume (ml) | | | | |
| N/a | 74.44 | 77.78 | 80.00 | 75 |
| Stroke Volume Variation (%) | | | | |
| N/a | 9 | 6 | 5 | N/a |

Stroke volume is the cardiac output divided by the heart rate. The stroke volume variation % is $(SV_{max}-SV_{min})/SV_{max}+SV_{min})\%$ across the respiratory cycle. SVV % is regarded as a continuous preload variable and, in combination with continuously measured cardiac output, defined a number of important characteristics of cardiac function facilitating optional fluid management. In this patient his resting cardiac output was 5.6 1/min—which is normal for an adult male. So it was assumed that his cardiac output was not low but he had very little functional exercise reserve i.e. on exercise the increased venous return did not produce a compensatory increase in stroke volume through the Starling mechanism. Thus even moderate exercise would lead to a right heart to left heart imbalance (in effect right heart success) in blood flow and dwelling of the blood on the post pulmonary left side of the heart. This would increase left arterial/ventricular filling pressures and then result in the classical CHF clinical symptoms of pulmonary oedema and breathlessness. The PulseCo System was able to show (via the continuous stroke volume and cardiac output traces) that the biventricular pacer restored synchrony (defined as the appearance of respiratory variation in haemodynamic parameters) at all pacer settings. So in this patient a variety of settings were able to at least improve left heart efficiency. In fact, this is not usually the case and in many CHF biventricular patients synchrony is only seen at a few of the rate/delay settings.

Therefore in this patient, as a variety of settings restored synchrony, the additional question to answer was which one of the settings was most likely to produce the required oxygen delivery whilst leaving the ventricle with additional capacity to respond to further increases in pre load? The results demonstrate the following:

1. Increasing AV delay increased the cardiac output modestly at both heart rates
2. Increasing the heart rate from 80 to 90 bpm increased cardiac output more than the delay changes
3. With both the higher heart rate and with increasing AV delay a reduction in pre load responsiveness, was observed—as assessed by the decrease in the parameter of stroke volume variation from 11% (e.g. at 80 bpm & delay of 100 msec) to 5% (at 90 bpm & a delay of 110 msec).
4. The conclusion was that this patient would have an adequate cardiac output and a higher functional reserve i.e. potential for response to the increased venous return associated with exercise at 80 bpm and at a AV delay of between 80–120 msec. The monitoring of beat to beat haemodynamic data allowed the choice of both rate and AV delay.

The invention claimed is:

1. A method of setting or adjusting a cardiac pacemaker in a patient diagnosed with cardiac asynchrony, which method comprises the steps of:
   i) implanting cardiac pacing wires into at least the right ventricle and the left ventricle of the heart of the patient,
   ii) continuously monitoring and recording the cardiac output, nominal stroke volume and/or arterial pressure of the patient on a beat-by-beat basis,
   iii) continuously monitoring and recording the respiratory cycle of the patient, and
   iv) adjusting the conduction delay between the electronic impulses to the cardiac pacing wires until a synchronization of respiratory changes with changes in the cardiac output, stroke volume or arterial pressure of the patient is obtained, wherein when the synchronization of respiratory changes with changes in the cardiac output, stroke volume or arterial pressure of the patient is obtained, the optimal setting of the pacemaker is then determined by monitoring the stroke volume or arterial pulse pressure variation of the heart and selecting a pacemaker setting which provides an increased ventricle pre-load responsiveness.

2. A method as claimed in claim 1 wherein a cardiac pacing wire is additionally implanted into the right atrium of the patient's heart.

3. A method as claimed in claim 1 wherein the arterial pressure of the patient is monitored by means of an arterial line and a pressure transducer.

4. A method as claimed in claim 1 wherein the nominal stroke volume is derived by a method comprises the steps of
   (a) recording and storing the arterial blood pressure waveform of a patient from a blood pressure monitoring device over a period of time;
   (b) subjecting the waveform obtained in step (a) to a non-linear transformation that corrects for the variation of the characteristics of the arterial system with pressure;
   (c) subjecting the corrected waveform from step (b) to autocorrelation in order to derive the pulsatility and heart rate of the corrected waveform; and
   (d) calculating the nominal stroke volume from the pulsatility.

5. A method as claimed in claim 4 wherein the transformation in step (b) is effected using a look up table with the mean of the date being found and substrated.

6. A method as claimed in claim 1 wherein the nominal stroke volume is derived by a method which comprises the steps of:

(e) recording and storing the arterial blood pressure waveform of a patient from a blood pressure monitoring device over a period of time;

(f) subtracting the mean of the waveform from step (e) and subjecting the data so obtained to autocorrelation;

(g) transforming the data from step (f) into data which relates to the pulsatility and heart rate of the waveform; and (h) calculating the nominal stroke volume from the pulsatility.

7. A method as claimed in claim 6 wherein the transformation in step (f) is effected using a look up table, with the mean of the data then being subtracted.

8. A method as claimed in claim 1 wherein the nominal stroke volume is derived by a method which comprises the steps of:

(i) recording and storing the arterial blood pressure waveform of a patient from a blood pressure monitoring device over a period of time;

(j) subjecting the data obtained in step (i) to Fourier analysis in order to obtain the modulus of the first harmonic; and (k) determining the nominal stroke volume from the modulus of the first harmonic obtained in step (j) and data relating to the arterial blood pressure and the heart rate.

9. A method as claimed in claim 1 wherein the nominal stroke volume is derived by a method which comprises the step of:

(l) recording and storing the arterial blood pressure waveform of a patient from a blood pressure monitoring device over a period of time;

(m) subjecting the waveform obtained in step (l) to a non-linear transformation that corrects for the variation of the characteristics of the arterial system with pressure;

(n) subjecting the data obtained in step (n) to Fourier analysis in order to obtain the modulus of the first harmonic;

(o) determining the nominal stroke volume from the modulus of the first harmonic obtained in step (n) and data relating to the heart rate and optionally the arterial blood pressure.

10. A method as claimed in claim 9 wherein the transformation in step (m) is effected using a look up table, with the mean of the data then being subtracted.

11. A method as claimed in claim 1 wherein the respiratory cycle of the patient is monitored by means of computer analysis of the arterial waveform, or by means of a strain gauge placed around the patient's chest.

12. A method as claimed in claim 1 wherein the conduction delay between the individual electronic impulses to the different cardiac pacing wires is adjusted systematically using a predetermined matrix.

13. A method as claimed in claim 1 wherein the cardiac output, nominal stroke volume and/or arterial pressure and the respiratory cycle of the patient are recorded and stored in an appropriately programmed computer and displayed on a display device integral with or connected to the computer.

14. A method as claimed in claim 1 wherein the pacing rate of the electronic impulses to the cardiac pacing wires may be varied.

15. A method as claimed in claim 14 wherein the pacing rate is varied between 80 and 100 beats per minute.

16. A method of adjusting a cardiac pacemaker having cardiac pacing wires implanted into at least the right ventricle and the left ventricle of the heart of a subject, which method comprises the steps of:

(x) continuously monitoring and recording the cardiac output, nominal stroke volume and/or arterial pressure of the subject on a beat-by-beat basis, (xi) continuously monitoring and recording the respiratory cycle of the patient, and (xii) adjusting the conduction delay between the electronic impulses to the cardiac pacing wires until a synchronization of respiratory changes with changes in the cardiac output, stroke volume or arterial pressure of the subject is obtained, wherein when the synchronization of respiratory changes with changes in the cardiac output, stroke volume or arterial pressure of the patient is obtained, the optimal setting of the pacemaker is then determined by monitoring the stroke volume or arterial pulse pressure variation of the heart and selecting a pacemaker setting which provides an increased ventricle pre-load responsiveness.

17. A method as claimed in claim 16 wherein the cardiac pacemaker includes a cardiac pacing wire implanted into the right atrium of the subject's heart.

18. A method as claimed in claim 16 where the respiratory cycle of the patient is monitored by means of computer analysis of the arterial waveform, or by means of a strain gauge placed around the patient's chest.

19. A method as claimed in claim 16 wherein the conduction delay between the individual electronic impulses to the different cardiac pacing wires is adjusted systematically using a pre-determined matrix.

20. A method as claimed in claim 16 wherein the cardiac output, nominal stroke volume and/or arterial pressure and the respiratory cycle of the patient are recorded and stored in an appropriately programmed computer and displayed on a display device integral with or connected to the computer.

21. A method as claimed in claim 16 wherein the pacing rate of the electronic impulses to the cardiac pacing wires may be varied.

22. A method as claimed in claim 21 wherein the pacing rate is varied between 80 and 100 beats per minute.

23. An apparatus for selling or adjusting a cardiac pacemaker in a patient diagnosed with asynchrony and having cardiac pacing wires implanted into at least the right ventricle and the left ventricle, which apparatus comprises:

(A) means for continuously monitoring and recording the cardiac output, nominal stroke volume and/or arterial pressure of the patient;

(B) means for continuously monitoring and recording the respiratory cycle of the patient;

(C) means for adjusting the delay between the electronic impulses to the pacing wires;

(D) means for determining when a synchronization of the respiratory changes with changes in the cardiac output, stroke volume or arterial pressure is obtained; and (E) means for determining the optimal selling of the pacemaker when the synchronization of respiratory changes with changes in the cardiac output, stroke volume or arterial pressure of the patient is obtained, wherein said means monitors the stroke volume or arterial pulse pressure variation of the heart and selects a pacemaker selling which provides an increased ventricle pre-load responsiveness.

* * * * *